United States Patent [19]

Boidin et al.

[11] 4,101,379

[45] Jul. 18, 1978

[54] ENZYME COMPLEX HYDROLYZING BACTERIAL MUCUS

[75] Inventors: Philippe Gerard Marie-Joseph Boidin, Phalempin; Raoul Louis Andre Cassaigne, Cappelle-en-Pevele; Bernard Albert Victor Colein, Houplin-Ancoisne; Robert Louis Felix Delecourt, Seclin, all of France

[73] Assignee: GB Fermentation Industries, Inc., Kingstree, S.C.

[21] Appl. No.: 756,669

[22] Filed: Jan. 4, 1977

[30] Foreign Application Priority Data

Jan. 22, 1976 [FR] France .............................. 76 01729

[51] Int. Cl.² ............................................. C12D 13/10
[52] U.S. Cl. ...................................... 195/62; 195/65; 195/2; 195/29
[58] Field of Search ..................... 195/62, 65, 66 R, 2, 195/4, 29

[56] References Cited

U.S. PATENT DOCUMENTS

| 3,868,303 | 2/1975 | Tsumura et al. | 195/2 |
| 3,890,198 | 6/1975 | Kobayashi et al. | 195/66 R |

Primary Examiner—Lionel M. Shapiro
Attorney, Agent, or Firm—Hammond & Littell

[57] ABSTRACT

A process for preparing complex enzymes capable of hydrolyzing bacterial mucus. A fermentation medium is inoculated with an appropriate bacterial species, fermentation of said medium is promoted while monitoring the development of complex enzymes in the fermentation medium and the fermentation is suddenly stopped when the activity of complex enzymes in the medium reaches its maximum. This process provides a reduction of viscosity of the fermentation must in the production of commercial enzymes and secondary metabolites.

6 Claims, No Drawings

ENZYME COMPLEX HYDROLYZING BACTERIAL MUCUS

BACKGROUND OF THE INVENTION

1. Field of Invention

The present invention relates to novel complex enzymes capable of hydrolyzing mucus released by bacteria in the course of their growth, the process for preparing said enzymes, and the use of these enzymes in reducing viscosity of fermentation musts in the commercial production of enzymes.

2. Prior Art

It is known that, in the course of the commercial production of enzymes and other secondary metabolites by bacilli, their secretion is generally accompanied with lysis of bacterial cell walls and/or release of highly polymerized complex polysaccharides into the growth medium. This results in a high increase of the viscosity of the fermentation must, whereby extraction and purification of the resulting enzymes are particularly uneasy.

Thus, the action of materials including peptidases, such as alanine amidase; glycosidases, such as muramidase, or lysozyme; and autolysins of a number of bacilli and bacteria capable of depolymerizing teichoric acids, causes degradation of the bacterial wall with release of high viscosity soluble products and submicroscopic particles. In addition to these products from degradation of the bacterial wall, the production medium of some bacterial enzymes also contains highly viscous polymers, generally polysaccharides, essentially comprising a chain of neutral polysaccharides, hexosamines and hexuronic acids.

The commercial fermentation of bacilli, particularly *Bacillus subtilis* and *Bacillis licheniform* is for the production of enzymes such as amylases, proteases, and the like, or of other metabolites, such as antibiotics, is thus generally accompanied with the occurrence of particulate products and highly viscous products in the fermentation medium, generally referred to as "mucus", the presence of which is quite troublesome from a technological point of view.

SUMMARY OF THE INVENTION

It has now been discovered that some bacilli secrete an enzyme complex capable of hydrolyzing the involved mucus much more rapidly than do autolysins. This results in a very important reduction of the viscosity of the fermentation must, whereby the further treatment of the latter and extraction of secondary metabolites are made substantially easier.

DETAILED DESCRIPTION OF THE INVENTION

One of the principal features of the involved enzyme complex is that it contains high endo-N-acetylhexosaminidase activity, quite specific of capsulartype polysaccharides present in the mucus and imparting a high viscosity thereto.

Among bacillary species capable of secreting the involved enzyme complex, *Bacillus subtilis,* which is commonly used in the production of enzymes and other secondary metabolites, is quite suitable for preparation of said complex.

A *Bacillus subtilis* strain secreting the enzyme complex of the invention, under particularly advantageous conditions, has been isolated and deposited at the American Type Culture Collection, Rockville, Maryland, U.S.A., under number 31,182.

It has been found that secretion of the enzyme complex, according to the invention, is initiated at a definite point of the growth of bacilli in the fermentation must, and then the enzyme activity increases rapidly, up to a maximum, after which it decreases rapidly, unless the production medium is stabilized. For stabilizing the production medium, ethylenediaminotetraacetic acid, sodium citrate, paramethylbenzene sulfofluoride, casein, parachlorometacresol, alone or in combination, may be used, for example.

It should be noted that secretion of the enzyme complex occurs at a point of growth of bacilli which does not correspond to that of the production for which they are generally grown.

Accordingly, the process according to the invention for producing the novel enzyme complex comprises essentially, after inoculating a fermentation medium with a suitable bacillus, monitoring the occurrence of the desired enzyme activity in the course of the fermentation process and introducing a stabilizer for this activity into the fermentation medium as soon as the considered enzyme activity has reached its maximum.

Then the enzyme complex is extracted from the fermentation medium and is purified and concentrated, if necessary.

According to the invention, the enzyme complex can be used for reducing viscosity of the fermentation must obtained in the production of commercial enzymes such as amylase and protease, or of metabolites such as antibiotics, by adding an appropriate amount of the enzyme complex to the fermentation medium and continuously stirring the medium until its viscosity drops to the desired value.

The activity of the enzyme complex in the fermentation medium is followed by measuring the reduction of viscosity of a standard mucus solution under the action of the involved enzyme activity. In order to give a value to this activity, an arbitrary unit is used, which is defined in such a manner that 1,000 units correspond to the amount of enzyme complex which, under assay conditions, is able to reduce by 15%, over 10 minutes, the viscosity of the mucus solution being used. The assay determination is carried out in a rotative viscosimeter of the standard type and the value is obtained by comparison with a reference product having the same source, so as to avoid the variation causes inherent to the complex nature of the substrate.

For purified products showing a high activity, it is advantageous to measure this activity as the number of strength units per milligram of protein-nitrogen, rather than as the number of strength units per gram of product.

The mucus active enzyme complex is produced by a selected strain of *Bacillus subtilis* showing the general features of the species, such as described in Bergey's "Manual of Determinative Bacteriology". The strain is maintained on a suitable medium containing a carbon source, and in the absence of oxygen (alkali pyrogallol method). The preculture medium contains a carbon source (liquefied starch), mineral salts and growth factors. The preculture medium is incubated after being inoculated with a culture on a supporting medium incubated in the presence of oxygen, at a temperature varying from 30° to 40° C, without stirring, to obtain, after four to seven days, more than 35% of free spores. This preculture medium is used for inoculating the production medium of the enzyme complex.

The production of the enzyme complex is carried out in a conventional, commercial fermentor.

Some embodiments of the invention are given hereafter by way of illustrating examples not limiting the scope of the invention.

EXAMPLE 1

The following fermentation medium was prepared:

|  | % by weight |
|---|---|
| Saccharified starch | 6 |
| Lactose | 0.3 |
| Dry yeast | 0.26 |
| Corn steep | 0.27 |
| Potassium sulfate | 0.3 |
| Magnesium sulfate heptahydrate | 0.017 |
| Sodium chloride | 0.033 |
| Manganese sulfate | 0.1 |
| Ammonium hydrogen phosphate | 0.5 |

A preculture medium of a carbon source (liquified starch), mineral salts and growth factors was inoculated with a culture of Bacillus substilis ATCC No No. 31,182 on a supporting medium and the resulting preculture was incubated in the presence of oxygen at 30° to 40° C without stirring to obtain after 4 to 7 days more than 35% of free spores. The preculture medium was then used to inoculate the fermentation medium.

After sterilization, pH was adjusted to pH 6.6, then fermentation was carried out as follows:

pH was allowed to drop from 6.6 to 5.8 and then kept between 5.8 and 6.0 with aqueous ammonia throughout fermentation.

Enzymatic activity was observed after eight to twelve hours of fermentation. This activity was fugacious and disappeared within 30 minutes after reaching its maximum level.

EXAMPLE 2

The same fermentation medium as in Example 1 was used, but pH was not adjusted during fermentation. Under these conditions, the enzymatic activity appeared either before the drop of pH to 5.8 or during the natural rise of pH following this drop.

EXAMPLE 3

The same fermentation medium as in Examples 1 and 2 was used, but a constant volume of a saccharified starch solution was added thereto every hour after the tenth hour of fermentation until occurrence of the enzyme complex in the fermentation medium. Under such conditions, the enzyme activity appeared after twelve hours of fermentation.

EXAMPLE 4

The same fermentation medium as in the precedent examples was used except that zinc sulfate was substituted for manganese sulfate. In this instance, the enzyme activity appeared before the final drop of pH.

EXAMPLE 5

The same fermentation medium as in Example 1 was used, except that liquefied starch was substituted for the saccharified starch. In this instance, the enzyme activity appeared either prior to the first adjustment of pH or after a few adjustments.

In order to stabilize the fermentation must, any method resulting in a quick stop of the fermentation process may be used. Accordingly, depending upon circumstances, one of the following methods can be used:

Quickly refrigerating the fermentation medium to 0° – 4° C.

Adding an agent for sequestering or chelating heavy metals; for example, 2.5 g/l ethylenediaminetetraacetic acid.

Adding an amount of proteins; for example, 25 g/l casein.

Stopping any fermentation by adding a bacteriostat or a bactericide; for example, 1 g/l parachlorometacresol.

Combining the preceding four methods (thus a satisfactory stabilization of enzyme, under a native liquid form, is obtained).

For isolating the enzyme complex, it is suitable to first remove the producing germs from the fermentation medium. This is obtained by flocculation. Then the floc is removed, the clarified phase is concentrated and the resulting concentrate is dried by atomization or freeze-drying.

The thus obtained enzyme preparation may be used per se or as a starting material in a further purification of the active agent.

A few non-limiting examples of purification and concentration of the enzyme complex are set forth hereafter.

EXAMPLE 6

To the stabilized fermentation must, the pH of which ranges between 6 and 7, was added, with stirring, from 2 to 20 ml/l of a cationic polyelectrolyte. Then 2 to 5% of a filter aid was added, then the mixture was filtered through a filter press or a vacuum rotating filter. The filrate was then concentrated in vacuo to about one-eighth of its initial volume. The concentrate was then atomized. Starting with a strength of 1,800 units per ml at the end of fermentation, a powder, assaying 22,000 strength units per gram, was recovered.

EXAMPLE 7

The procedure of Example 6 was repeated but the floc was removed by centrifugation instead of filtration.

EXAMPLE 8

The procedure of Examples 6 and 7 was repeated, but the clarified solution was concentrated by ultrafiltration. An enzyme powder assaying 60,000 strength units per gram was thus obtained.

EXAMPLE 9

The procedure of examples 6 and 7 was repeated but after clarification the enzyme complex was precipitated by adding thereto ammonium sulfate to a concentration equivalent to 55% saturation, the pH being kept at 6.10. The precipitate was recovered by centrifugation and dried under vacuum to an assay of 80,000 strength units per gram. It is also possible to incorporate an adjuvant into the precipitate, to recover the mixture on a filter press and to dry it under vacuum.

EXAMPLE 10

Starting with a powder obtained according to the process disclosed in Examples 6 and 7, and having an activity of 114 strength units per milligram of nitrogen, a formulation having a high endo-N-acetylhexosaminidase activity and a high depolymerizing activity against the mucus substrate can be obtained. To produce such a formulation, the following purification technique was used: the enzyme complex was dissolved into water, the active fraction was precipitated by addition of an equal volume of acetone at −5° C to the solution previously obtained and kept at a pH between 6 and 7, the precipitate was recovered by centrifugation and dissolved in a 0.15 M phosphate buffer of pH 6.7, the enzyme was applied on a column of hydroxylapatite equilibrated with a 0.15 M phosphate buffer of pH 6.7, the enzyme was eluted with 0.15 M phosphate buffer of pH 6.7, the eluate was concentrated by ultrafiltration the concentrate was subjected to a molecular filtration through Sephadex G 200 or Biogel P 200 gel, and the active enzyme was dried by freeze-drying.

Under these conditions, a purified formulation was obtained, the activity of which was 47,800 strength units per milligram of protein nitrogen. The optimum activity of this formulation was obtained at pH 3.5 and 37° C; more generally, this formulation had a measurable activity in a pH range from 5 to 8.5 and in a temperature range from 10° to 60° C. This activity was not enhanced by the presence of metal ions.

It will be shown hereafter in which manner the enzyme complex according to the invention, containing endo-N-acetylhexosaminidase, can be used to reduce the viscosity of fermentation musts, including *Bacillus subtilis* or *Bacillus licheniformins*.

EXAMPLE 11

By adding 10,000 strength units of enzyme complex to one liter of *Bacillus subtilis* fermentation must having a high amylase activity, over 12 hours and at 15° C, its viscosity was reduced from 60 centipoises to 8.6 centipoises.

EXAMPLE 12

By adding 10,000 strength units of enzyme complex per liter of *Bacillus licheniformis* fermentation must, having a high proteolytic activity, over 12 hours at 14° C, its viscosity was reduced from 55 centipoises to 9.5 centipoises.

EXAMPLE 13

By adding 15,000 strength units of enzyme complex per liter of *Bacillus subtilis* fermentation must, the pH ranging between 6 and 7 and the temperature being kept constant at 40° C, the following variation of viscosity was recorded:

| Time | | |
|---|---|---|
| 0 | 32 | centipoises |
| 1 hour | 12 | centipoises |
| 2 hours | 7.5 | centipoises |
| 3 hours | 6.25 | centipoises |
| 10 hours | 4.5 | centipoises |
| 13 hours | 4.5 | centipoises |

What we claim is:

1. A process for preparing complex enzymes capable of hydrolyzing bacterial mucus, comprising the following steps: inoculating a fermenatation medium with a Bacillus subtilis ATCC No. 31,182, causing fermentation of said medium while monitoring development of said complex enzymes in the fermentation medium, and suddenly stopping fermentation when the activity of complex enzymes in the medium reaches its maximum.

2. A process according to claim 1, wherein complex enzymes are extracted from the fermentation medium after stabilization of the latter.

3. A process according to claim 1, wherein fermentation is stopped by quickly refrigerating the fermentation medium to 0° − 4° C.

4. A process according to claim 1 wherein fermentation is stopped by adding to the fermentation medium one of the following products: an agent for sequestering or chelating heavy metals, a protein or a bacteriostat or a bactericide.

5. An enzyme complex capable of hydrolyzing bacterial mucus and containing a high endo-N-acetylhexosaminidase activity and produced by the process of claim 1.

6. Use of the enzyme complex according to claim 5 for the reduction of viscosity of the fermentation must in the production of commercial enzymes and secondary metabolites.

* * * * *